United States Patent
Gaudl et al.

(10) Patent No.: US 9,982,150 B2
(45) Date of Patent: May 29, 2018

(54) OLIGOMERIC AMINOKETONES AND THEIR USE AS PHOTOINITIATORS

(71) Applicant: SUN CHEMICAL CORPORATION, Parsippany, NJ (US)

(72) Inventors: Kai-Uwe Gaudl, Bavaria (DE); Jürgen Dieker, Darmstadt (DE)

(73) Assignee: Sun Chemical Corporation, Parsippany, NJ (US)

(*) Notice: Subject to any disclaimer, the term of this patent is extended or adjusted under 35 U.S.C. 154(b) by 0 days. days.

(21) Appl. No.: 14/906,100

(22) PCT Filed: Jul. 8, 2014

(86) PCT No.: PCT/US2014/045750
§ 371 (c)(1),
(2) Date: Jan. 19, 2016

(87) PCT Pub. No.: WO2015/023371
PCT Pub. Date: Feb. 19, 2015

(65) Prior Publication Data
US 2016/0160061 A1    Jun. 9, 2016

Related U.S. Application Data

(60) Provisional application No. 61/864,730, filed on Aug. 12, 2013.

(51) Int. Cl.
*C09D 11/101*    (2014.01)
*C08F 2/50*    (2006.01)
*C07C 225/22*    (2006.01)
*C09D 11/037*    (2014.01)
(Continued)

(52) U.S. Cl.
CPC .......... *C09D 11/101* (2013.01); *C07C 225/22* (2013.01); *C08F 2/50* (2013.01);
(Continued)

(58) Field of Classification Search
CPC ... C09D 11/101; C09D 11/107; C09D 11/037; C07C 225/22; C08F 2/50; C08F 222/18; C08F 2222/205; C08F 2222/225
See application file for complete search history.

(56) References Cited

U.S. PATENT DOCUMENTS 4,347,111 A    8/1982  Gehlhaus et al.
5,888,481 A *  3/1999  Horn ............... C07C 255/41
                                                        424/59

(Continued)

FOREIGN PATENT DOCUMENTS

CN    101243109 A    8/2008
CN    101326250 A    12/2008
(Continued)

OTHER PUBLICATIONS

International Search Report issued in International Application No. PCT/US2014/045750 dated Oct. 22, 2014.
(Continued)

*Primary Examiner* — Michael F Pepitone
*Assistant Examiner* — Jessica M Roswell
(74) *Attorney, Agent, or Firm* — Charles C. Achkar; Ostrolenk Faber LLP.

(57) ABSTRACT

The invention relates to photoactive oligomeric aminoketones of general Formulae I and II, for compositions and inks curable with ultraviolet (UV) light. The oligomeric aminoketones of the general Formula I are made by condensation of aminoketones with aldehydes, and aminoketones of the general Formula II are made by acylation of aromatic amines with phthalic anhydride, followed by esterification with a polyol. The aminoketones provide good curability of energy curable coatings and inks with UV-A light, and are proposed for photoinitiator systems for low migration inks.

8 Claims, 3 Drawing Sheets

UV-Absorption Spectrum of Example 3 (in THF)

(51) Int. Cl.
  *C09D 11/107* (2014.01)
  *C08F 222/18* (2006.01)
  *C08F 222/20* (2006.01)
  *C08F 222/22* (2006.01)

(52) U.S. Cl.
  CPC .......... *C09D 11/037* (2013.01); *C09D 11/107* (2013.01); *C08F 222/18* (2013.01); *C08F 2222/205* (2013.01); *C08F 2222/225* (2013.01)

(56) References Cited

U.S. PATENT DOCUMENTS

| | | |
|---|---|---|
| 2008/0213502 A1 | 9/2008 | Romagnano et al. |
| 2009/0176914 A1 | 7/2009 | Gotoh |
| 2010/0143274 A1 | 6/2010 | Deshayes et al. |

FOREIGN PATENT DOCUMENTS

| | | |
|---|---|---|
| WO | WO 2004/052837 A2 | 6/2004 |
| WO | WO 2011/030089 A1 | 3/2011 |

OTHER PUBLICATIONS

Written Opinion of the International Searching Authority issued in International Application No. PCT/US2014/045750 dated Oct. 22, 2014.
International Preliminary Report issued in International Application No. PCT/US2014/045750, dated Feb. 16, 2016.
Chinese Office Action issued in Chinese Application No. 201480044040.4, dated Dec. 7, 2016 (with English Translation).
European Patent Application 14 83 6326.0 dated Jun. 21, 2017.

* cited by examiner

OLIGOMERIC AMINOKETONES AND THEIR USE AS PHOTOINITIATORS

CROSS REFERENCE TO RELATED APPLICATIONS

The present application is a § 371 National Phase application based on PCT/US2014/045750 filed Jul. 8, 2014, which claims the benefit of U.S. Provisional Application No. 61/864,730 filed Aug. 12, 2013 the subject matter of each of which is incorporated by reference in their entirety.

FIELD OF THE INVENTION

The present invention relates to oligomeric aminoketones that are useful as photoinitiators in UV-curable coatings and inks. The oligomeric aminoketones of the invention are particularly useful for coatings and inks to use for printing or coating materials wherein a low migration of photoinitiators is required, such as food packaging.

BACKGROUND

Radiation curable compositions containing acrylic acid ester groups can be cured by exposure to ultraviolet light (UV). For a fast curing composition, a photoinitiator is necessary, which forms radicals under irradiation with photons and initiates free-radical polymerization of the acrylate groups, which then leads to a hardening (curing) of the product. Aldehyde-ketone photoinitiators are described in US 2009/0048363.

However, radiation curable compositions containing photoinitiators can be a challenge for several applications in packaging, especially in food packaging ("Radiation curing in packaging", Radtech Report March/April 2006). Residual photoinitiators, as well as their cleavage products, remain in the coating or ink and may cause problems, such as for example migration, contamination, odor or off taste. For example, residues of photoinitiators and cleavage products can migrate through the substrate and affect adjacent products such as food stuff or may contaminate food by off set contact migration. Therefore, there is a continuous search for photoinitiator systems which have low potential for migration and odor.

As described in the literature (L. L. Katan in "Migration of additive food contact", Black Academical & Professional, first edition, London 1996, page 97, table 5.3), the ability of a material to migrate is governed by its molecular weight, rather than by its chemical structure. Therefore, for a low migration UV-curable ink or coating, photoactive components having a molecular weight of >500-1,000 Daltons are preferred.

Oligomeric and polymeric tertiary aromatic amines are used in the art to enhance the UV-curing response of radiation curable compositions ("Industrial Photoinitiators", CRC press London 2010, page 106). Together with ketones, they can form type-II photoinitiators. Tertiary amines are especially useful for the surface cure of UV-inks and UV-coatings as they are able to transform non-reactive oxo-radicals, which are deactivated by reaction with oxygen, into more reactive radicals and reduce the inhibiting effect of oxygen on the polymerization on the surface of inks and coatings, ("Photoinitiators for free radical and cationic & anionic photo-polymerization", Wiley & Sons 1998, page 84).

Moreover, unlike type-I photoinitiators, type-II photoinitiators usually do not form small molecules (splitting products) and are therefore especially useful in applications requiring low migration of chemical species.

Among the most reactive amines proposed for low migration applications are oligomeric aminobenzoates. Examples of oligomeric aminobenzoates for low migration applications are, for example, Genopol AB-1 and AB-2 (products of Rahn Group, Switzerland) and Omnipol ASA (product of IGM Resins, Netherlands). However, aminobenzoates still need a partner to form an effective initiator system, such as an aromatic ketone or thioxanthone.

In contrast, aromatic aminoketones, besides the tertiary amino group, already contain an aromatic ketone, which can be excited by UV-light and additionally contribute to UV-cure. An example of an oligomeric aminoketone for low migration applications is Omnipol SZ (IGM Resins).

Moreover, due to recent developments of UV-bulbs emitting predominantly in the UV-A area, and which do not produce ozone and exhibit a low energy consumption, there is a constant search for photoactive materials especially useful for UV-A curing to make the UV-technology safer in relation to both migration and process safety.

SUMMARY OF THE INVENTION

The present invention provides novel oligomeric aminoketones according to general Formulae I and II, shown below. In certain embodiments, the oligomeric aminoketones are useful as photoinitiators in UV-curable compositions. In other embodiments, the UV-curable compositions are UV-curable coatings or inks. The oligomeric aminoketones are particularly useful for printing or coating materials wherein a low migration of chemical species is required.

In a certain aspect, the present invention provides novel aminoketones of the general Formula I:

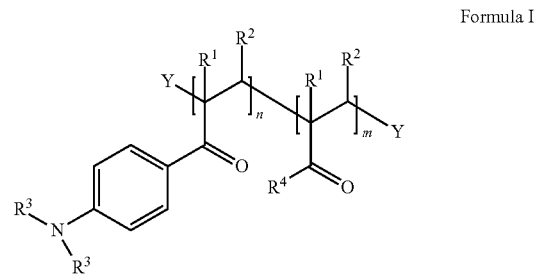

Formula I wherein
$R^1$ and $R^2$ are each independently selected from the group consisting of H, a branched or unbranched $C_{1-12}$ alkyl, and a $C_{3-12}$ aryl radical;
Each $R^3$ is independently selected from a branched or unbranched $C_{1-12}$ alkyl, or $C_{3-12}$ cycloalkyl radical; each of which is independently optionally substituted with $R^7$;
$R^4$ is selected from the group consisting of a branched or unbranched $C_{1-12}$ alkyl, $C_{3-12}$ aryl, and $C_{3-12}$ cycloalkyl radical; each of which is independently optionally substituted with $R^7$;
each $R^7$ is independently selected from the group consisting of oxygen, nitrogen, and sulfur;
Each Y is a chain ending group, independently selected from H, or a methylol group;
n denotes an integer from 1-50; and
m denotes an integer from 0-50.

In another aspect, the present invention provides novel aminoketones of the general Formula II:

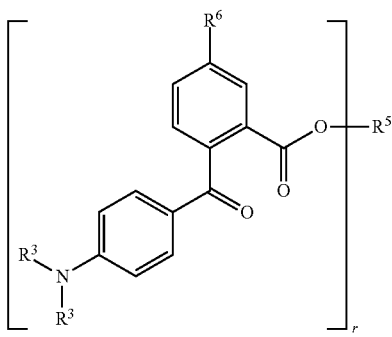

Formula II wherein
Each $R^3$ is independently selected from branched or unbranched $C_{1-12}$ alkyl, or $C_{3-12}$ cycloalkyl radical; each of which is independently optionally substituted with $R^7$;
$R^5$ is selected from the group consisting of a di-, tri-, tetra-, penta- and hexavalent alkyl radical, which is optionally substituted by oxygen;
$R^6$ is selected from the group consisting of H, a branched or unbranched $C_{1-12}$ alkyl, and a $C_{3-12}$ aryl radical;
each $R^7$ is independently selected from the group consisting of oxygen, nitrogen, and sulfur; and
r denotes an integer from 2-6.

In one embodiment, the present invention provides novel compositions comprising one or more aminoketones of any one of Formulae I or II, and one or more acrylates.

In one embodiment, the present invention provides novel UV-curable coatings or inks comprising one or more aminoketones of any one of Formulae I or II, and one or more acrylates.

In another embodiment, the UV-curable coatings or inks are curable with UV light having a wavelength of 310-400 nm.

In certain embodiments, the UV-curable coatings or inks further comprise a colorant.

In certain embodiments, the UV-curable coatings or inks comprising an aminoketone according to Formula II are capable of being cured by a light emitting diode (LED).

In another embodiment, the UV-curable coatings or inks comprising an aminoketone according to any one of Formulae I or II comprise no splitting type photoinitiators.

In a certain embodiment, the present invention provides low migration printed material comprising a UV-curable coating or ink according to any one of Formulae I or II.

In another embodiment, the cured material is obtained by curing with UV radiation curing of the UV-curable coatings or inks described above.

DETAILED DESCRIPTION OF THE INVENTION

Figure 1:
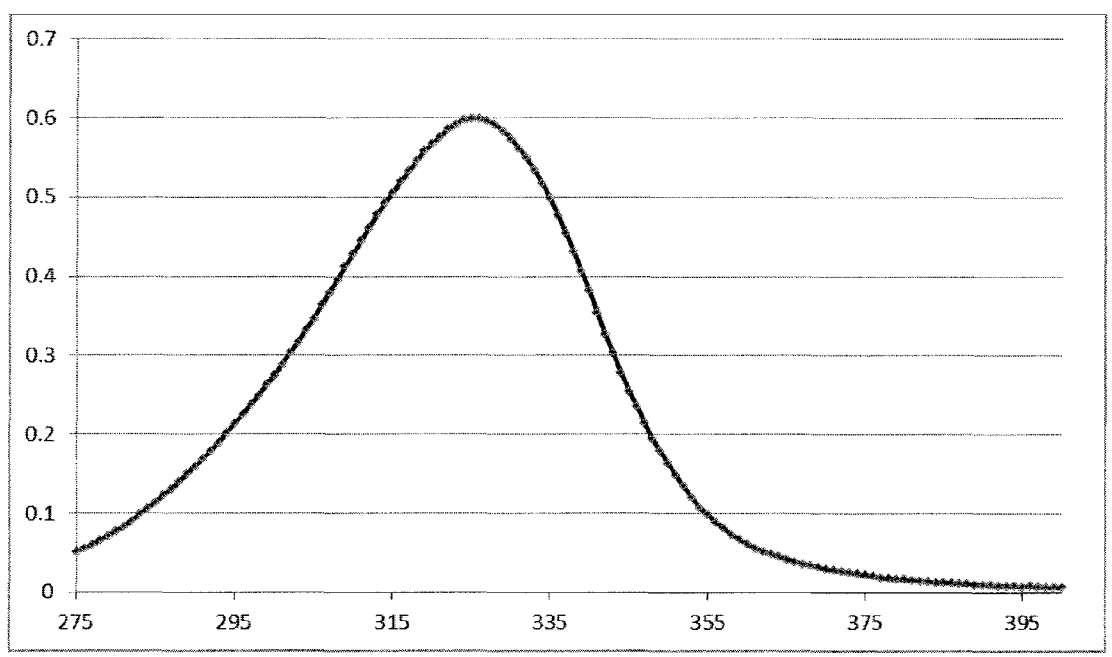
FIG. 1: Shows the UV absorption spectra of the aminoketone composition of Example 3.

The present invention relates to photoactive oligomeric aminoketones for compositions curable with ultraviolet (UV) light. More specifically, the photoactive oligomeric aminoketones are suitable for radiation curable low migration printing inks and coatings.

It is an object of the present invention to provide effective oligomeric aminoketones which are useful in photoinitiator systems, especially for low migration coatings and inks.

In a certain aspect, the present invention provides novel aminoketones of the general Formula I:

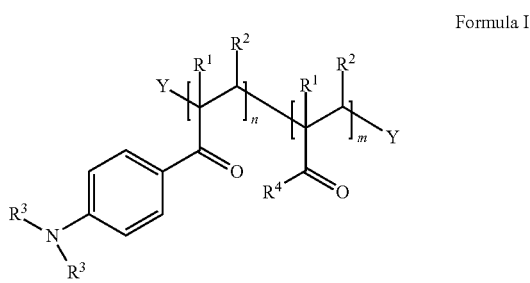

Formula I wherein
$R^1$ and $R^2$ are each independently selected from the group consisting of H, a branched or unbranched $C_{1-12}$ alkyl, and a $C_{3-12}$ aryl radical;
Each $R^3$ is independently selected from branched or unbranched $C_{1-12}$ alkyl, or $C_{3-12}$ cycloalkyl radical; each of which is independently optionally substituted with $R^7$;
$R^4$ is selected from the group consisting of a branched or unbranched $C_{1-12}$ alkyl, $C_{3-12}$ aryl, and $C_{3-12}$ cycloalkyl radical; each of which is independently optionally substituted with $R^7$;
$R^7$ is selected from the group consisting of oxygen, nitrogen, and sulfur;
Each Y is a chain ending group, independently selected from H, or a methylol group;
n denotes an integer from 1-50; and
m denotes an integer from 0-50.

In another aspect, the present invention provides novel aminoketones of the general Formula II:

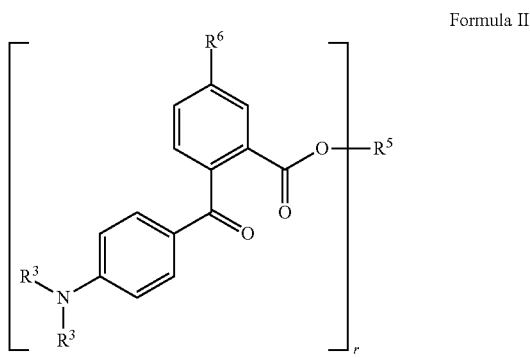

Formula II wherein
Each $R^3$ is independently selected from branched or unbranched $C_{1-12}$ alkyl, or $C_{3-12}$ cycloalkyl radical; each of which is independently optionally substituted with $R^7$;
$R^5$ is selected from the group consisting of a di-, tri-, tetra-, penta- and hexavalent alkyl radical, which is optionally substituted by oxygen;
$R^6$ is selected from the group consisting of H, a branched or unbranched $C_{1-12}$ alkyl, and a $C_{3-12}$ aryl radical;

R⁷ is selected from the group consisting of oxygen, nitrogen, and sulfur; and
r denotes an integer from 2-6.

The aminoketones of general Formula II preferably show an ultraviolet absorption maxima of 325 nm to 365 nm, and a high reactivity in radiation curable coatings and inks. The aminoketones of Formula II are further preferably curable by UV-A radiation.

The aminoketones of the general Formula I can be made by a simple condensation reaction of aromatic aminoketone monomers with aliphatic aldehydes, especially with formaldehyde, as depicted below.

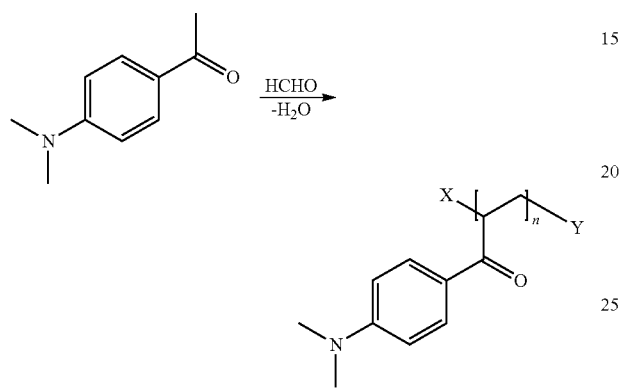

Examples of suitable ketones for making the compounds of the general Formula I are N,N-dimethylamino-acetophenones, N,N-diethylamino-acetophenones, N,N-dipropylamino-acetophenones, N,N-dibutylamino-acetophenones, 4-piperidino-acetophenones, 4-morpholino-acetophenones, N-methyl-N-phenyl aminoacetophenones, acetyl-N-methylcarbazoles, acetyl-N-ethylcarbazoles, acetyl-N-alkylindoles, acetyl-N-alkyldehydroindoles, 3-acetyl-N-ethyl-carbazol and N-ethyl-3-acetylindol preferred are N,N-dimethyl-4-aminoacetophenone, 4-morpholino-acetophenone, N-methyl-N-phenyl-4-aminoacetophenone. Example structures of such ketone monomers include, but are not limited to:

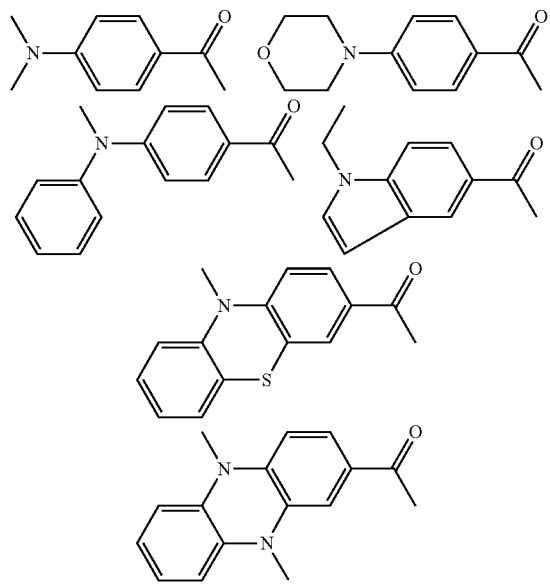

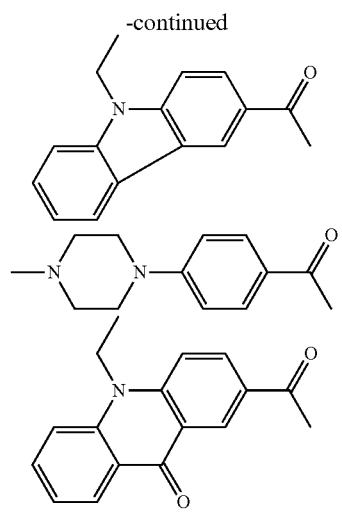

Suitable ketone monomers are commercially available, or can be prepared by Friedel-Crafts acylation of aromatic compounds with acetic anhydride or acetylchloride, as described in the literature (Organikum, Wiley-VHC, 22$^{nd}$ edition, page 380).

Examples of suitable ketone co-monomers include acetone, methyl ethyl ketone, heptan-2-one, pentan-3-one, methyl isobutyl ketone, cyclopentanone, cyclohexanone, methyl cyclohexanone, acetophenone, methyl acetophenone, ethyl acetophenone, propiophenone, tert-butyl-acetophenone, cyclohexyl-acetophenone, phenylacetophenones, acetylfluorene, methyl naphthyl ketone, hydroxynaphthyl ketone, preferred are acetophenone and 4-phenyl acetophenone.

The co-monomers are not necessarily required, but provide properties such as solubility and compatibility, and can provide, in some cases, an additional increase of UV-reactivity, as described herein.

The condensation of the aldehydes and ketones usually takes place under alkaline conditions. Strong alkaline bases, such as, for example, potassium or sodium hydroxide or methoxides and the like are most common. Quaternary ammonium salts are applied for particularly high melting resins. Condensation preferably takes place at temperatures between 25-100° C. and is otherwise described in the literature (see for example, Journal of Applied Polymer Science, Vol. 50 (1996) pages 577ff; and Journal of Applied Polymer Science, Vol. 60 (1996) pages 465ff).

The required formaldehyde is usually used in the form of an approximately 30 weight % aqueous solution of formaldehyde, or in the form of solid para-formaldehyde. After synthesis, the polymers are purified to remove non-reacted monomers, and residues of bases and formaldehyde, preferably by washing with hot water or treatment with steam, and finally dried.

The obtained compounds of the general Formula I are colorless to yellow solids, and exhibit a weight-average molecular weight (Mw) within the range of 500-3,000, preferably 1,000-1,500, and are soluble in the most common organic solvents. The aminoketones preferably have an ultraviolet absorption maxima in the range of 325-365 nm, a molar extinction coefficient of 12,000-30,000 liter·mol$^{-1}$·cm$^{-1}$, and a good fit with the emission of typical UV-bulbs used for the curing with UV-A light.

As described earlier, the aminoketones are able to initiate a photo polymerization, whereas the aminobenzoates are not UV-effective alone. A UV-curable composition of a comparative aminobenzoate (Example 2) and the amino ketone of the general Formula I (Example 3) in trimethylol propane triacrylate were made by dissolving the comparative aminobenzoate from Example 2 and the inventive aminoketone of Example 3 in trimethylol propane triacrylate (SR 351 from Sartomer company USA) by stirring at slightly elevated temperature (30-45° C.) and allowing to cool down to room temperature. The coatings were applied onto Bykocharts "Opacity Chart PA-2810" (Byk) using a K-Control Coater (Erichsen) at a coating weight of about 10 g/m². The compositions were UV-cured by with an iron doped mercury bulb having a power of 160 W/cm, at a belt speed of 20 meter/minute, at 50% power. The UV-curable composition containing the aminoketone was cured to a tack-free finish after two passes, whereas the aminobenzoate composition remained uncured and tacky after two passes, as shown in Table 1.

Evaluation of Through Cure and Surface Cure:

Through Cure Evaluation—

The standard thumb twist test to confirm adequate cure was used, where a thumb is firmly applied to the cured film and twisted. Any deformation of the film, tackiness of the film, or transfer of the film to the thumb is classified as a failure. Such a test is well known in the art and is, for example, described on page 74 of Test Methods for UV and EB Curable Systems, C. Lowe & P. K. T Oldring, SITA Technology, 1994, ISBN 0 947798 07 2.

Surface Cure Evaluation—

The term "tack-free" or "dry" means that talc or other powder which is applied to the cured film does not adhere to the surface when blown or lightly brushed or shaken to remove any talc. The percentage of talc adhering to the surface of inventive coating 2, from Example 3, was compared to the percentage of talc adhering to the surface of a curable composition known to have excellent surface cure. Curable compositions containing benzophenone and an amine-synergist are known to have excellent surface cure. The curable composition known to have excellent surface cure was made according to Example 2, except that 0.6 g benzophenone was added. This composition shows excellent surface cure when UV-cured in two passes with an iron doped mercury bulb having a power of 160 W/cm, at a belt speed of 20 meter/minute, at 50% power. If the percentage of talc adhering to an experimental curable composition (e.g. inventive composition 2 from Example 3, or comparative aminobenzoate of Example 2) exceeded the amount of talc adhering to the curable composition known to have excellent surface cure, the result was negative. The test is described on page 75 of Test Methods for UV and EB Curable Systems, C. Lowe & P. K. T Oldring, SITA Technology, 1994, ISBN 0 947798 07 2.

The print is considered to be fully cured when the print is dry and no thumb print or surface marking is left after the test.

TABLE 1

Compositions and UV-curing results

| Composition | SR351 [g] | Oligomeric amine [g] | Through cure | Surface Cure |
|---|---|---|---|---|
| 1 (comparative) | 10 | 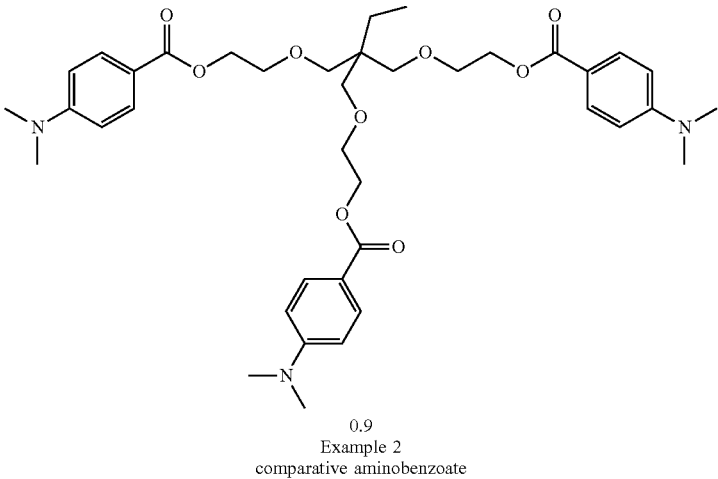<br>0.9<br>Example 2<br>comparative aminobenzoate | fail | tacky |
| 2 (inventive) | 10 | 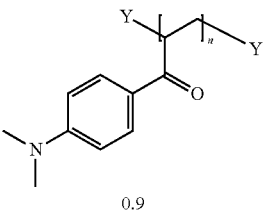<br>0.9<br>Example 3 | good | tack free |

SR 351 = trimethylol propane triacrylate from Sartomer company, USA

FIG. 1 shows the absorption spectra of a compound of the general Formula I (Example 3). It is clearly visible that the aminoketone of Example 3 is able to catch more UV-A (310-400 nm) light from an iron doped mercury bulb than commercially available aminobenzoates and aminoketones. Example 3 is, moreover, able to catch light from the very important UV-bulb radiation emission at 365 nm, in contrast to the commercial aminobenzoate Genopol AB-1 and the commercial aminoketone Omnipol SZ, which cannot absorb light at 365 nm. The increased UV-A light absorption of the composition of Example 3 results in an improved through cure and surface cure, as shown in Table 1.

The performance of an oligomeric aminoketone of the general Formula I was compared to oligomeric aminobenzoates and a commercial oligomeric aminoketone. The compositions were cured with one pass with an iron doped mercury bulb having 160 W/cm, at 50% power, and a belt speed belt speed of 30 m/min. Coating weight was ~10 g/m². The substrate was Byko-chart cardboard "Opacity Chart PA-2810" (Byk). The results are shown in Table 2.

The compositions in Table 2 were made and tested similarly to those in Table 1, but as the compositions contain benzophenone, in order to see an effect, the applied UV-dose was lowered (higher belt speed and only one pass).

TABLE 2

Compositions and UV-curing results

| Composition | SR351 [g] | Oligomeric amine [g] | Omnipol BP [g] | Through cure | Surface cure |
|---|---|---|---|---|---|
| 3 (comparative) | 10 | 0.5 Example 1 comparative aminobenzoate | 0.5 | good | tacky |
| 4 (comparative) | 10 | 0.5 Example 2 comparison aminobenzoate | 0.5 | good | slt. tacky |
| 5 (comparative) | 10 | 0.5 Omnipol SZ (IGM) comparison aminoketone | 0.5 | good | tacky |

TABLE 2-continued

Compositions and UV-curing results

| Composition | SR351 [g] | Oligomeric amine [g] | Omnipol BP [g] | Through cure | Surface cure |
|---|---|---|---|---|---|
| 6 (inventive) | 10 | 0.5 Example 3 | 0.5 | good | tack free |

SR 351 = trimethylol propane triacrylate from Sartomer company USA
Omnipol BP = oligomeric benzophenone derivative from IGM resins, Netherlands.
Omnipol SZ = oligomeric aminoketone derivative from IGM resins, Netherlands The results from Table 2 indicate that composition 6 with the inventive aminoketone (Example 3) has improved surface cure vs. both the commercial aminoketone Omnipol SZ and the di- and trifunctional aminobenzoates from Examples 1 & 2.

Surprisingly, although commercial Omnipol SZ is an aminoketone as well, which absorbs in the UV-A region, the presence of the acetyl group and the low amine functionality apparently make such a material not superior to the tested oligomeric aminobenzoates.

It was furthermore surprisingly found that if the aforementioned amino ketones, suitable for making the materials of the general Formula I, are co-condensed with aromatic ketones, such as acetophenone, methoxy acetophenones, 4-phenoxy acetophenone or 4-phenyl acetophenone, the UV-reactivity is largely enhanced, as depicted below.

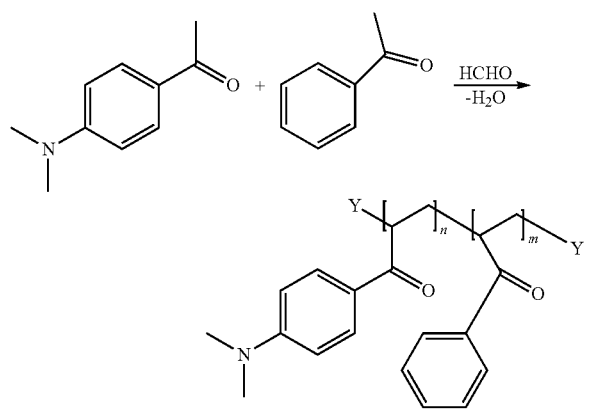

To demonstrate the reactivity of these oligomeric initiators, experimental UV-curable black low migration inks were made. Black inks are the most difficult inks to UV-cure because black pigments absorb UV-light at any wavelength, and that UV-light is then not available to activate an initiator system.

For making a low migration ink, which is suitable for food packaging, the risk of migration of components of the ink into food must be minimized. Generally acknowledged and described in the prior art, the tendency of a chemical to migrate is a function of mobility and molecular weight.

Therefore, in a low migration ink, migrating low molecular weight monomeric photoinitiators are either minimized or completely replaced by oligomeric or polymeric photoinitiators.

Moreover, to minimize the risk of migration of acrylate monomers, even in the case of incomplete cure, monomers with the highest acrylate functionality and molecular weight are preferred, such as di-trimethylol propane hexaacrylate, ethoxylated pentaerythritol tetraacrylate, dipentaerythritol hexaacrylate and ethoxylated dipentaerythritol hexaacrylate, available from suppliers such as Cytec and Arkema Company. Thus, even if only one of four or six acrylate groups polymerizes, the whole molecule is anchored in the crosslinked acrylate matrix and can no longer migrate.

The UV-curing performance of low migration black inks from Example 8 were measured by a "set-off" test. Black prints of UV-cured samples, which were printed with a comparable density, were covered with a white counter paper. Then, with a pressure of 10 tons, the printed substrate and the counter paper were pressed together. Then, the counter paper was removed from the print and the amount of transferred ink on the counter paper was measured by a densitometer. As a rule, the lower the amount of transferred ink, the lower the readings on the densitometer, and the better cure. The results are shown in Table 3. For clarity, only the modified photoinitiator blend was given in Table 3 and the effect on UV-curing. The full formulation is given in Example 8.

The inks were printed onto Byko-charts "Uncoated Chart PA2831" (Byk) using an IGT C5 proofer to densities of 1.75 to 1.85 (black), and cured using a Fusion UV H-bulb with 33 mJ/cm$^2$ (up to four passes).

Figure 2:
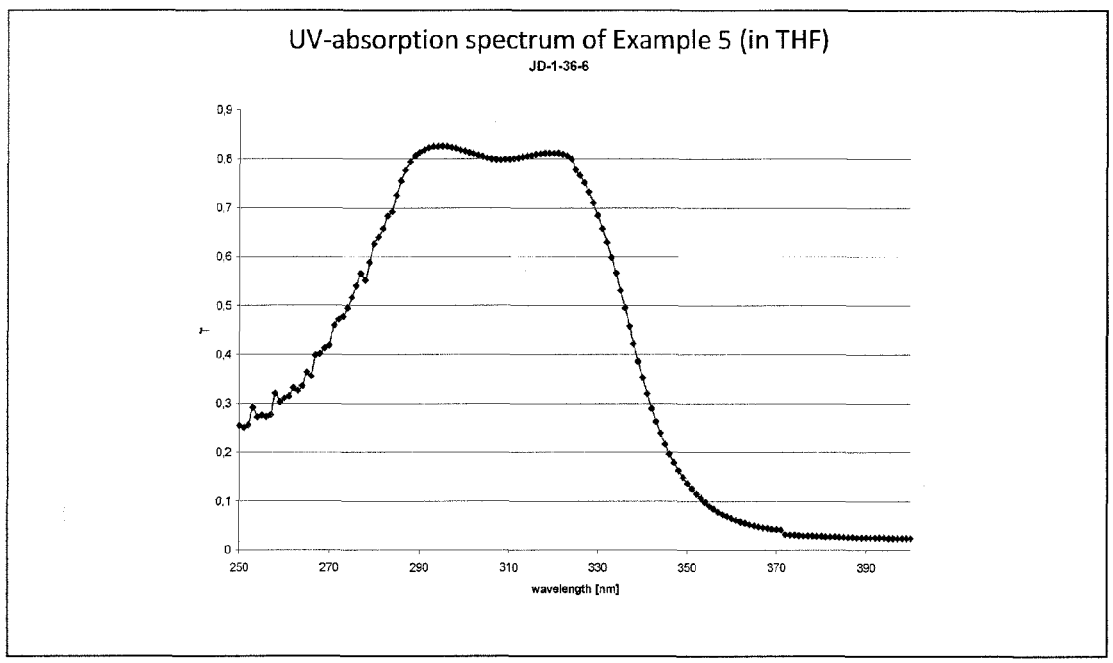
FIG. 2: Shows the UV absorption spectra of the aminoketone composition of Example 5.

The data in Table 3 indicate, by the result of the comparable values of the UV-curing test, that black low migration inks comprising aminoketones of the general Formula I (Inks 2 & 3 with inventive aminoketones of Examples 4 & 5) can be UV-cured without Irgacure 369 (which is known to be among the most reactive photoinitiators for black inks) and, moreover, also in the absence of aminobenzoates. The strong and broad absorption from 290-360 nm of such an aminoketone can also be seen in the UV absorption spectrum of Example 5 (see FIG. 2).

TABLE 3

Cure of low migration black inks (Full formulation is given in Example 8)

| Photoinitiator blend | Ink 1 (STD) Wt. % | Ink 2 Wt. % | Ink 3 Wt. % |
|---|---|---|---|
| Oligomeric aminoketone | — | Example 5 14.0 | Example 4 23.0 |
| Low migration photoinitiator blend (Sun Chemical) based on oligomeric deritives of aminobenzoates, benzophenones and thioxanthones | 9.1 | — | — |
| Irgaacure 369 (BASF) | 2.1 | — | — |
| Oligomeric sensitizer (IGM) | 4.8 | 4.8 | 4.8 |
| UV-Curing test energy | | Amount of set off in units of optical density | |
| 33 mJ/cm$^2$ | 0.85 | 0.83 | 0.77 |
| 67 mJ/cm$^2$ | 0.50 | 0.72 | 0.95 |
| 100 mJ/cm$^2$ | 0.12 | 0.11 | 0.32 |
| 133 mJ/cm$^2$ | 0.08 | 0.07 | 0.08 |

Therefore, the present invention also provides energy curable inks that do not contain splitting type-I photoinitiators. The absence of splitting type-I photoinitiators in experimental black inks 2 & 3 in Table 3, such as, for example, 2-benzyl-2-dimethylamino-2-(4-morpholinophenyl)-butane-1-one (Irgacure 369, BASF), has the advantage that no small molecules are formed during the initiation of radical polymerization. This considerably reduces the risk of migration.

In the last few years, due to the development of doped UV light bulbs emitting at longer wavelengths in the UV-A area, at 310-400 nm, and the development of high powered light emitting diodes (LED) emitting at 365-395 nm, it has become more and more attractive to commercially use such light sources because there is no ozone formation, and lower energy consumption, so that this technology is regarded as a "greener" solution.

However, there is a limited source of oligomeric photo-reactive materials having light absorption in the UV-A area, especially in the region of 365-395 nm of light emitting diodes (LED).

Therefore, the invention also provides oligomeric aminoketones of the general Formula II, having longer wavelength absorption maxima >340 nm, and overlapping with the emission of LED bulbs.

The oligomeric aminoketones of the general Formula II can be made, for example, by a Friedel-Crafts acylation of aromatic amines with phthalic anhydride or acid chlorides followed by esterification with a multifunctional alcohol.

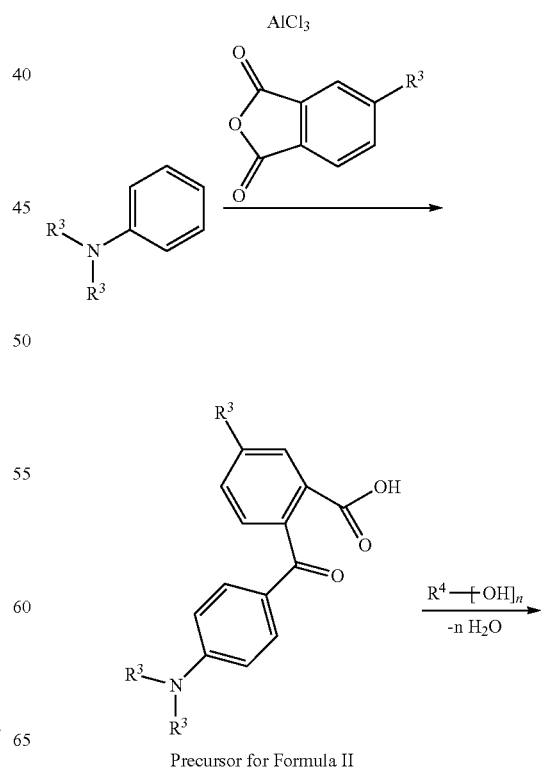

Precursor for Formula II

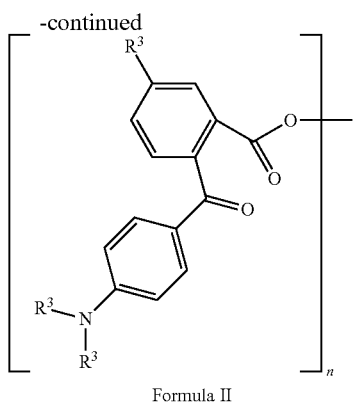

Formula II

General methods of acylation are described in the literature (Organikum, Wiley-VHC, 22$^{nd}$ edition, page 380). Usually, amine and anhydride, and an optional solvent, are dissolved in each other and aluminum trichloride is added, so that the temperature does not exceed 30° C. Then, the reaction is allowed to complete, and the mixture is poured into acidified water. Then, the precipitated solid is collected, filtered, washed, and dried. The intermediate acids are colorless to slightly pale yellow to faint greenish solids, which are soluble in the common solvents, as well as alkaline water. This also offers the possibility to purify the intermediate acids by dissolving in alkaline water and precipitation by acidification with an acid such as diluted sulfuric acid.

Figure 3:
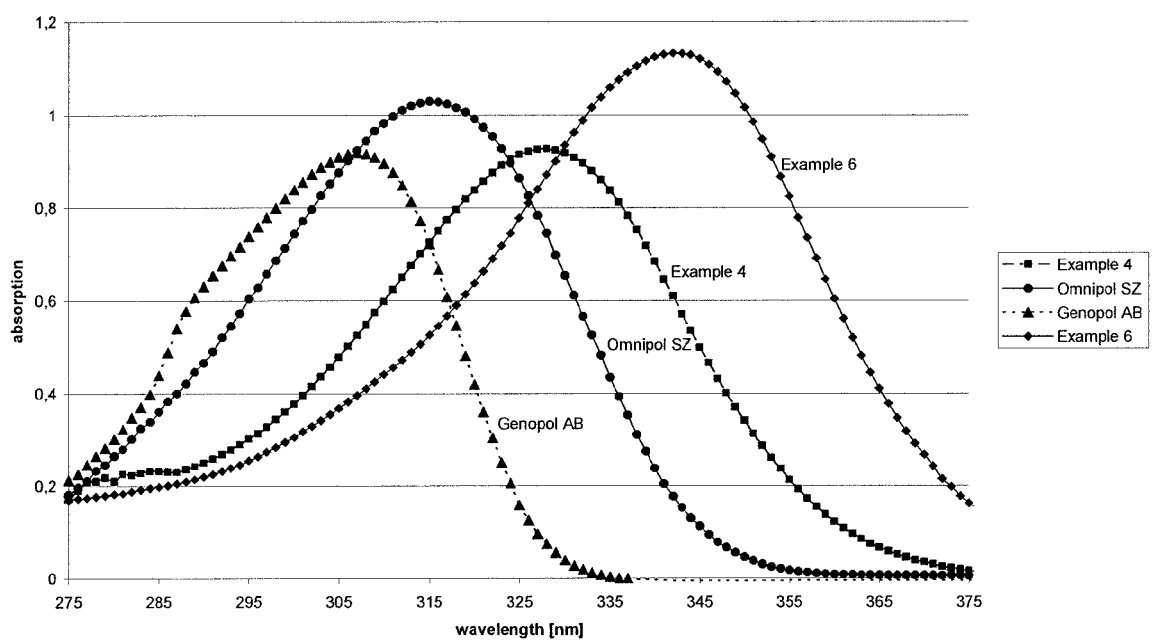
FIG. 3: Shows the comparative UV absorption spectra of the novel aminoketone compositions of Examples 4 and 6, and two commercially available photoinitiators, Omnipol BP, and Genopol AB.

FIG. 3 shows the absorption spectra of a precursor compound of the general Formula II (Example 6). It is clear that the aminoketone is able to catch light from a doped mercury bulb having strong emission in UV-A light area of 310-400 nm. Compositions comprising the aminoketone will therefore have improved through cure and surface cure properties.

Then, in a final step, the acids are esterified with alcohols, preferably with di-, tri-, tetra, penta- and hexavalent polyols such ethylene glycol, 1,4-butandiol, 1,6-hexandiol, dipropylene glycol, neopentylglycol, ethoxylated neopentylglycol, propoxylated neopentylglycol, tripropylene glycol, ethoxylated bisphenol-A, poly(ethylene)glycol, trimethylolpropane, ethoxylated trimethylolpropane, propoxylated trimethylolpropane, propoxylated glycerol, pentaerythritol, ethoxylated pentaerythritol, propoxylated pentaerythritol, alkoxylated pentaerythritol, ditrimethylolpropane, dipentaerythritol, dipentaerythritol or mixtures thereof, preferred are ethoxylated trimethylolpropanes, ethoxylated pentaerythritols and propoxylated pentaerythritol, and the like.

Usually an acid catalyst, such as methane sulfonic acid or sulfuric acid, or a metal catalyst, such as titanium tetrabutylate or butyl tin hydroxyoxide, is suitable. The formed water can be removed physically by the help of an entrainer such as toluene, a nitrogen gas stream, vacuum, or chemically by the reaction with a water up-taking chemical, such as a carbodiimide.

Alternatively, the esterification can also be done with a multifunctional epoxide, such as bisphenol A-diglycidyl ether, under catalysis with triphenylphosphine or an ammonium salt, such as tetraethylammonium bromide. The products are highly viscous, pasty to solid yellow to brownish materials, having a molecular weight of 500 to 2,000 Daltons, an absorption maximum of 340-375 nm, and a molar extinction coefficient of 10,000-35,000 liter·mol$^{-1}$·cm$^{-1}$.

As an example for photoactivity of an oligomeric aminoketone of the general Formula II, two compositions were made with the compound of Example 7. Composition 7 was made without Omnipol BP, while composition 8 included Omnipol BP. The compositions were made by dissolving the oligomeric aminoketone in trimethylol propane triacrylate at elevated temperatures (50-60° C.) until clear solutions were obtained. The compositions were applied at a coating weight of ~10 g/m$^2$, on a Byko-chart "Opacity Chart PA-2810" (Byk) cardboard. The compositions were cured with an iron doped mercury bulb having 160 W/cm at 50% power, and at a belt speed of 20 m/min. The compositions and the results of the UV curing are shown in Table 4.

TABLE 4

Compositions and UV-curing results

| Composition | SR351 [g] | Oligomeric amino ketone [g] | Omnipol BP [g] | Through cure | Surface cure |
|---|---|---|---|---|---|
| 7 | 10 | Example 7 0.8 | — | good | good |

TABLE 4-continued

Compositions and UV-curing results

| Composition | SR351 [g] | Oligomeric amino ketone [g] | Omnipol BP [g] | Through cure | Surface cure |
|---|---|---|---|---|---|
| 8 | 10 | Example 7<br>0.5 | 0.4 | good | good |

The results obtained with Composition 7 show that a material of general Formula II (Example 7) is able to start and proceed to photopolymerization as the sole initiator. Often, in commercial photoinitiator blends, amino-compounds are mixed with benzophenone derivatives to enhance cure. Such an example is shown with Composition 8, where the oligomeric aminoketone is used in combination with the oligomeric benzophenone Omnipol BP, retaining the good curing properties though less aminoketone is used.

The aminoketones of the general Formulae I and II are useful in radiation curable compositions which can be UV-cured by an actinic light source, such as UV-light, provided by a high-voltage mercury bulb, a medium-voltage mercury bulb, a xenon bulb, a carbon arc lamp, a metal halide bulb, an UV-LED lamp, or sunlight. The wavelength of the applied irradiation is within a range of 310 to 500 nm, preferably 320 to 395 nm.

Due to the high molar extinction coefficients of the aminoketones of the general Formulae I and II, they are especially suitable for radiation curable printing inks, such as, for example, a UV-flexographic ink, a UV-jet ink, a UV-gravure ink or a UV-offset ink. The high extinction coefficient also allows UV-curing in highly pigmented systems, in which pigments and photoinitiators are competitors for the available UV radiation. The inks are made according to the methods known in the art, such as, for example, dispersing a pigment in the radiation curable compositions of this invention with a bead mill or a three roll mill until the desired particle size and color strength is achieved.

The energy curable inks may contain one or more colorants in the form of a dye or pigment dispersed therein. Pigments suitable for use in the present invention include conventional organic or inorganic pigments. Representative pigments may, for example, be selected from the group of Pigment Yellow 1, Pigment Yellow 3, Pigment Yellow 12, Pigment Yellow 13, Pigment Yellow 14, Pigment Yellow 17, Pigment Yellow 63, Pigment Yellow 65, Pigment Yellow 73, Pigment Yellow 74, Pigment Yellow 75, Pigment Yellow 83, Pigment Yellow 97, Pigment Yellow 98, Pigment Yellow 106, Pigment Yellow 111, Pigment Yellow 114, Pigment Yellow 121, Pigment Yellow 126, Pigment Yellow 127, Pigment Yellow 136, Pigment Yellow 138, Pigment Yellow 139, Pigment Yellow 174, Pigment Yellow 176, Pigment Yellow 188, Pigment Yellow 194, Pigment Orange 5, Pigment Orange 13, Pigment Orange 16, Pigment Orange 34, Pigment Orange 36, Pigment Orange 61, Pigment Orange 62, Pigment Orange 64, Pigment Red 2, Pigment Red 9, Pigment Red 14, Pigment Red 17, Pigment Red 22, Pigment Red 23, Pigment Red 37, Pigment Red 38, Pigment Red 41, Pigment Red 42, Pigment Red 48:2, Pigment Red 53:1, Pigment Red 57:1, Pigment Red 81:1, Pigment Red 112, Pigment Red 122, Pigment Red 170, Pigment Red 184, Pigment Red 210, Pigment Red 238, Pigment Red 266, Pigment Blue 15, Pigment Blue 15:1, Pigment Blue 15:2, Pigment Blue 15:3, Pigment Blue 15:4, Pigment Blue 61, Pigment Green 7, Pigment Green 36, Pigment Violet 1, Pigment Violet 19, Pigment Violet 23, Pigment Black 7, and the like.

The radiation curable compositions and inks of this invention may contain the usual additives to modify flow, surface tension, gloss and abrasion resistance of the cured coating or printed ink.

Such additives contained in inks or coatings typically are a surface-active agent, a wax, or a combination thereof. These additives may function as leveling agents, wetting agents, slip agents, dispersants and de-aerators. Preferred additives include fluorocarbon surfactants, silicones, organic polymer surfactants, and inorganic materials such as talc.

Examples include the Tegorad™ product lines (commercially available from Tego Chemie, Essen, Germany) and the Solsperse™ product lines (commercially available products from Lubrizol Company).

The radiation curable compositions of the present invention may optionally contain small amounts of additional type-I and type-II photoinitiators such as, for example, benzophenones, benzylketals, dialkoxy acetophenones, hydroxyalkylacetophenones, aminoalkylphenones, acylphosphinoxides and thioxanthones, for example benzophenone, methylbenzophenone, 4-phenylbenzophenone, 4,4'-bis(dimethylamino)-benzophenone, 4,4'-bis(diethylamino)-benzophenone, 2,2-dimethoxy-2-phenylacetophenone, dimethoxyacetophenone, diethoxyacetophenone, 2-hydroxy-2-methyl-1-phenylpropan-1-one, 2-benzyl-2-dimethylamino-1-(4-morpholinophenyl)-butan-1-one, 2-methyl-1-[4(methoxythio)-phenyl]-2-morpholinopropan-2-one, diphenylacylphenyl phosphinoxide, diphenyl(2,4,6-trimethylbenzoyl)phosphinoxide, 2,4,6-trimethylbenzoylethoxyphenyl phosphinoxide, 2-isopropylthioxantone, 4-isopropylthioxanthone, 2,4-dimethylthioxanthone and their oligomeric counterparts.

The substrate to be printed upon may be composed of any typical substrate material such as paper, plastics, metals, and composites. The substrate may be print stock typically used for publications or may be a packaging material in the form of a sheet, a container such as a bottle or can, or the like. In most instances, the packaging material is a polyolefin such as a polyethylene or a polypropylene, a polyester such as polyethylene terephthalate, or a metal such as an aluminum foil, a metalized polyester, or a metal container.

The radiation curable compositions of the present invention are especially suitable for such applications in which no small molecules which have the tendency to migrate or are suspected to cause health risks, are present. Such applications are, for example, the coating of (food) packaging articles where especially small photoinitiator molecules are undesirable.

Once the energy curable composition is applied to the packaging material, it may be used to contain any kind of liquid or solid material such as foods, drinks, cosmetics, biological materials or specimens, pharmaceuticals, etc.

EXAMPLES

The following examples illustrate specific aspects of the present invention and are not intended to limit the scope thereof in any respect and should not be so construed.

Molecular Weight Determination:

Molecular weight was measured by Gel Permeation Chromatography (GPC) using three GPC columns (manufactured by PSS (Polymer Standards Service-USA, Inc.), SDV 5 μm 1000 Å, SDV 5 μm 500 Å, SDV 5 μm 100 Å, at a flow rate of 1.0 ml/min, eluted with tetrahydrofuran (THF), and at a column temperature of 40° C., mono-disperse polystyrene equivalent molecular weight calibration. A differential refractive index detector (RI) and a UV-detector (254 nm) were used. The dispersability (Mw/Mn) was calculated from the measurement results.

UV-Spectra Measurement:

Spectra were acquired using a Unicam UV-2 UV/VIS spectro-photometer. All absorption spectra were obtained using 1 cm cuvettes, scanning within the 200-800 nm range. Solutions were prepared in a 100 ml volumetric flask, and, if required, subsequently diluted so that a maximum absorbance of less than 2 was obtained. From the absorption the molar extinction coefficient was calculated in liter·mol$^{-1}$·cm$^{-1}$.

FTIR Spectra Measurement:

The Fourier transform infrared (FTIR) spectra were recorded on a Bio-Rad Excalibur FTS 3000 spectrophotometer using a surface reflectance method (solid samples, Golden Gate single reflection diamond attenuated total reflectance accessory).

Melting Point:

Melting points were determined by a calibrated Büchi melting point apparatus.

Example 1 (Comparative): Synthesis of an Oligomeric Difunctional Aminobenzoate 20.4 g (0.105 mol) of tetraethylene glycol was dissolved in 38.6 (0.20 mol) of N,N-dimethylaminobenzoic acid ethylester (EDB) at 80-100° C. Then, 1.0 ml of titanium isopropylate was added and the reaction mixture was heated under Nitrogen to 170° C. for three hours. Then vacuum (20 hPa) was applied for 30 minutes. A brown clear liquid remained. After several days, the liquid crystallized to a pale amber solid.

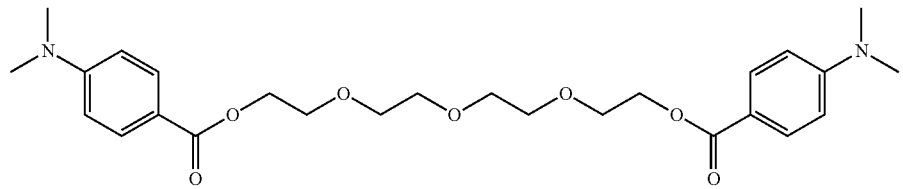

Yield:
47.2 g (96%)
Characterization:
Molecular weight: Number average: 478; Weight average: 492
Purity: 98 area % (GPC)
Melting point: 48-52° C.
Absorption maximum: 308 nm Example 2 (Comparative): Synthesis of Oligomeric Trifunctional Aminobenzoate

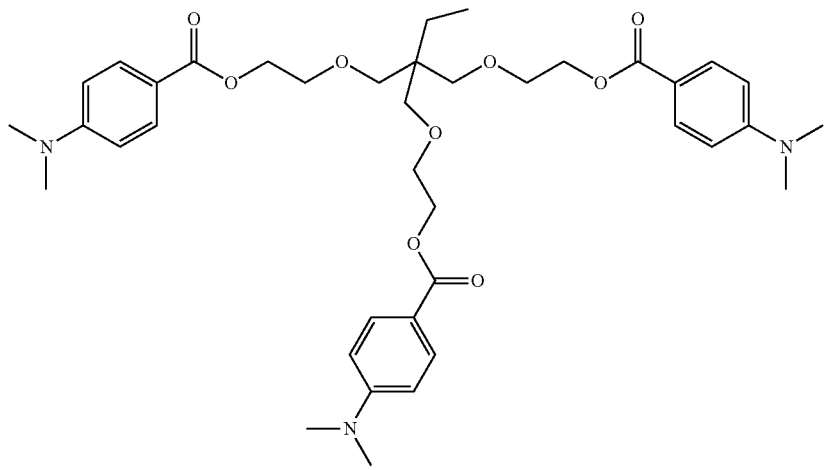

55.0 g of N,N-dimethylaminobenzoic acid ethylester (EDB) and 45.0 g of ethoxylated trimethylolpropane (Mw average ~450) were charged into a 250 ml flask, equipped with thermometer, mechanical stirrer, nitrogen inlet tube, condenser and receiver. Nitrogen was introduced at a rate of three bubbles/sec. Then, the mixture was heated to 60° C. until the EDB was completely into solution. Then, 1.5 g of titanium iso-propylate (Tyzor TPT) was added, the mixture was heated to 150-170° C., and ethanol was distilled off. After the ethanol formation subsided, the reaction was resumed for another 3-5 hours at 170° C. to minimize the residual amount of EDB.
Yield:
87.8 g.
Characterization:
Residual: EDB 0.1% determined by quantitative GC
Molecular weight: Number average 943; Weight average 973
Purity: 96 area % (GPC)
Viscosity: 20.5 Pas@25° C. (D=50 l/s)
Absorption maximum: 310 nm Example 3: Synthesis of an Aminoketone of the General Formula I

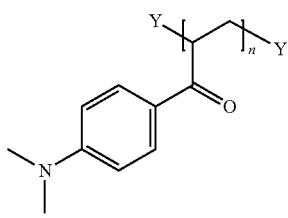

wherein n and Y are as defined above.

40.8 g (0.25 mol) 4-dimethylamino acetophenone, 175 ml (4.3 mol) of methanol and 6.7 ml (7.3 g; 0.09 mol) of formalin (37% strength in water) were introduced to a four-necked flask and heated therein, with stirring and under a nitrogen atmosphere, to 60-65° C. 8.0 g of sodium hydroxide solution (25% strength in water) were added, and the reaction mixture heated up to 67° C. Over 30 minutes, 12.3 ml (13.4 g, 0.165 mol) of formalin (37% strength in water) were added and the reaction mixture was heated to 69-75° C. and held under reflux for 5 h. Then, methanol and water were distilled off. The obtained mixture was washed with warm water (200 ml, 80° C.) by intense stirring and the washing media was decanted when cooled to 45° C. This washing procedure was repeated three times. The obtained yellow resin was dried in vacuum.

Optionally, the resin was re-precipitated by drop-wise addition of a 20% resin solution in ethyl acetate to methanol resulting in a slightly yellow precipitate. The obtained solid was filtered, washed with methanol and dried.
Characterization:
Molecular weight: Number average 469; Weight average 580
IR: (cm-1): 2893, 2867, 2809, 1653, 1587 (vs), 1547, 1525, 1482 (w), 1432, 1364, 1277, 1230, 1182, 1163 (s), 1117, 1063, 1005, 942, 819, 762, 691 (w)
Absorption maximum: 325 nm Example 4: Synthesis of an Aminoketone of the General Formula I

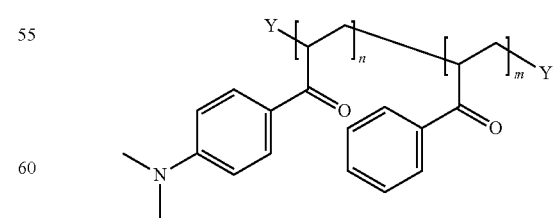

wherein n, m, and Y are as defined above; and the molar ratio between n and m is 1:1.

245.0 g (1.5 mol) of 4-(dimethylamino)acetophenone, 180 g (1.5 mol) of acetophenone, 600 ml (14.8 mol) of methanol and 88.0 g (0.18 mol) of formaldehyde solution (37% strength in water) were placed in a four-necked flask and heated with stirring under a nitrogen atmosphere to 60-65° C., resulting in a clear solution.

96 g of 25 wt. % strength sodium hydroxide solution (0.6 mol) were added and the reaction mixture was heated to 67-70° C. During a period of 45 minutes, 148 ml (161 g, 1.98 mol) of formaldehyde solution (37% strength in water) was added, and the reaction mixture was then heated to 69-75° C. and held under reflux for 5 h. Methanol/water was removed by condensation up to an inner temperature of the refluxing media of 81° C. (~540 ml collected).

The obtained resin was washed with boiling water (1000 ml) and the washing media was decanted when cooled to 65° C. This washing procedure was repeated until the washing water was neutral. The obtained solid was dried and powdered.

For optional further purification, the dried resin was dissolved in a small amount of an appropriate solvent, e.g. ethyl acetate. The turbid, yellow solution was filtered. The clear filtrate was precipitated by drop-wise addition of the solution to methanol (1000 ml methanol for 100 g) resulting in a pale yellow precipitate. The obtained solid was filtered and dried, resulting in 350 g of a pale yellow, clear, and brittle resin.

Characterization:
Molecular weight: Number average 714; Weight average 921
Color: 2 Gardner (50% in toluene)
IR-spectroscopy: (cm$^{-1}$): IR: (cm-1): 3058, 2911, 2857, 2814, 1661 (s), 1590 (vs), 1547, 1527, 1482 (w), 1441, 1368, 1320, 1233, 1182 (sh), 1167 (s), 1105, 1001, 941, 821, 789, 762, 696 (vs)
Absorption maximum: 328 nm (in THF)

Example 5: Synthesis of an Aminoketone of the General Formula I

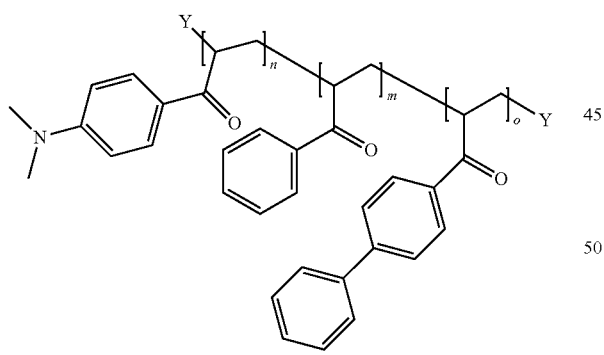

wherein n, m, and Y are as defined above;
is an integer from 1-50; and
the molar ratio of n:m:o is 1:1:1.

49.1 g (0.25 mol) of 4-acetylbiphenyl, 30.0 g (0.25 mol) of acetophenone, 40.8 g (0.25 mol) of 4-dimethylamino acetophenone, 35 ml of ethanol, 0.25 g of benzyltriethylammonium chloride, and 11.2 ml of 37 wt. % aqueous formaldehyde solution in water were placed into a four-necked flask equipped with a mechanical stirrer, inner thermometer, dropping funnel (sodium hydroxide solution and later formaldehyde solution), and a reflux condenser equipped with a distilling controller dividing the reflux. The substances were heated therein with stirring to ~80° C. in an inert nitrogen atmosphere, resulting in a yellow clear solution. 18.8 g (0.19 mol) sodium hydroxide solution (40 weight % in water) was added drop wise to the reaction mixture at 70° C. An exothermic reaction started heating the mixture to about 78° C., resulting in a yellow, slightly turbid reaction mixture. Over 20 minutes, 45 ml (0.6 mol) of formalin (37% strength in water) were added at 75-80° C. The reaction mixture was then heated to reflux for 2 h. Solvent was removed by condensation using a distilling controller dividing the reflux (one drop removed per two seconds) up to an inner temperature of 90° C. After 2 h of reflux, about 42 ml of solvent was removed resulting in a higher viscosity of the reaction mixture. For complete reaction, a third part of formalin was added at an inner temperature of about 94° C. Reflux was continued for about 20 minutes up to an inner temperature of 107° C. No further solvent evaporated. In sum, 57 ml of solvent was collected. Heating was stopped and the resin cooled down to 97° C. For neutralization, 51.3 g of a 22 wt % acetic acid solution in water (11.25 g; 0.1875 mol; 10.7 ml of 100% acetic acid in 40 ml water) was added slowly to the molten resin while stirring. At 90° C. the resin started so solidify. The pH-value of the washing "water" was determined to be 6 to 7. The water was separated by decantation. The resin was heated to 85-95° C. and washed with 300 ml water twice. The water was separated by decantation each time and the pH-value was measured to be ~5. Residuals were removed by re-precipitation of the dissolved resin (120 g in 120 ml ethyl acetate) from methanol (1.1 l). The crude product was fritted using a glass fit with pore size (D2) and dried in vacuum.

Yield:
125 g, after re-precipitation: 90 g grayish solid
Characterization:
Molecular weight: Number average 1150; Weight average 1770
IR-spectrum: (cm-1): 3048, 2928, 1666 (s), 1589 (vs), 1543, 1439, 1367, 1229, 1180, 946, 820, 741 (s), 691 (vs);
UV-spectrum: concentration=27.5 mg oligomer/liter Example 6: Precursor for Synthesis of Aminoketones of the General Formula II

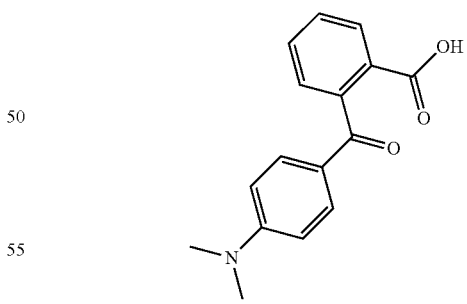

29.0 g of N,N-dimethylaniline, 29.6 g of phthalic anhydride, and 100 ml of benzene was dispersed, and treated in portions with 52.0 g of aluminum trichloride, so that the temperature did not exceed 25° C. Then, the mixture was stirred at room temperature for 1 hour, then at 55-60° C. for 30 minutes. Then, the mixture was cooled to room temperature and treated with 60 ml of 20% sulfuric acid. The solvent was decanted from the precipitate and the precipitate was dispersed in 1 l of water. The water was treated with 6 g of sodium hydroxide solution (6 g sodium hydroxide in 60 ml). The precipitated greenish solid was collected by filtration, to give 27 g of raw product.

Purification:

The raw product was dispersed in 500 ml of water and the pH was adjusted to 8-9. Then, the aqueous solution was filtered and acidified to pH 6-7, when a small amount of a greenish solid by-product precipitated, which was disposed. Then, the solution was acidified to pH 3-4, at which a white solid precipitated, which was filtered, washed with water and dried.

Yield:
23.5 g

Characterization:
Melting point: 209-211° C.
Purity (gas chromatography): 99% (trimethylsilyl derivatized)
Purity (GPC) 99%
Absorption maximum: 342 nm
Molar extinction coefficient: 33,800 [liter·mol$^{-1}$·cm$^{-1}$]

Example 7: Synthesis of an Aminoketone of the General Formula II

Characterization:
GPC: 85 area % difunctional (UV-detector); 12 area % monofunctional (UV-detector)

Example 8: Lithographic UV-Curable Black Inks

Varnishes:

Two varnishes were made from aminoketone resins, from Examples 4 and 5 (varnishes 2 and 3), and one varnish was made from a ketone resin (varnish 1). All were dissolved in ethoxylated pentaerythritol tetraacrylate and stabilized with a polymerization inhibitor. The composition and viscosity of the varnishes are shown in Table 5.

Inks:

From varnishes 1-3, black lithographic inks 1-3 were made on a Buehler three roll mill at 30° C., with a pressure of 1.5 MPa, with 2 passes.

UV Curing Test Method (Set-Off Test):

Directly after UV cure, the reverse face of a board substrate (incada exel or silk—3×3 cm2) was applied on the cured ink sample. Both were introduced on a press and a pressure of 10 t was applied. The print was released as soon as the pressure was reached. The set-off material on the board substrate was measured with a densitometer and compared to the standard. The results are shown in Table 6.

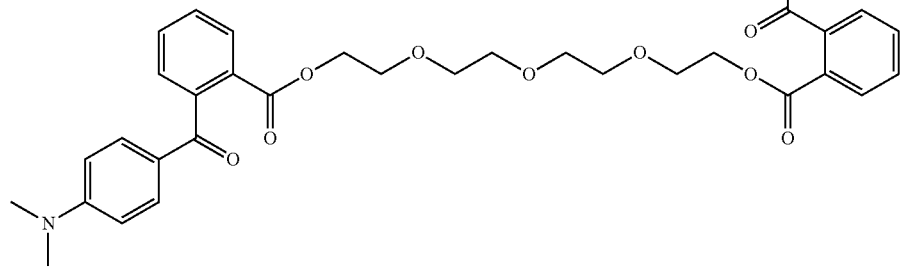

13.5 g (0.05 mol) of product of Example 6 was mixed with 9.65 g (0.0245 mol) of tetraethylene glycol and 50 mg of butyltinhydroxide-oxide. Then, the reaction mixture was heated under a Nitrogen stream at 190° C. for five hours. A dark brown clear liquid remained.

Yield:
21.5 g

Viscosity:

Viscosity was measured with a Cone & Plate Physika 300 Rheometer at 25° C. (D=2-1001/s).

Tack:

Tack was measured with a calibrated "Tack-o-scope" (1 ml ink at 30° C. held for 90 seconds at 50 rpm, then 30 seconds at 300 rpm. Then, the tack value was taken at 150 rpm.

TABLE 5

Composition and properties of varnishes

| Starting materials: | Varnish 1 (comp) [%] | Varnish 2 [%] | Varnish 3 [%] |
|---|---|---|---|
| Mixture of tetra- and hexafunctional acrylates (3:1) | 53.0 | 53.0 | 51.0 |
| Stabilizer (Rahn) | 1.0 | 1.0 | 1.0 |
| Ketone resin (Leuna) | 46.0 | — | — |

TABLE 5-continued

Composition and properties of varnishes

| Starting materials: | Varnish 1 (comp) [%] | Varnish 2 [%] | Varnish 3 [%] |
|---|---|---|---|
| 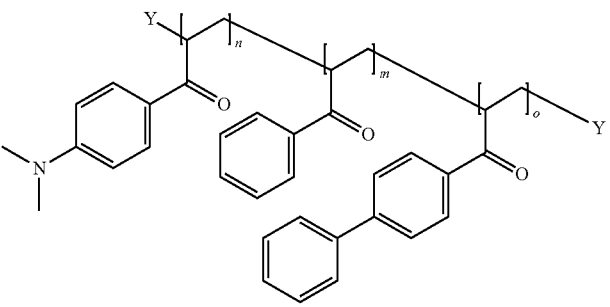 Example 4 | — | — | 48.0 |
| 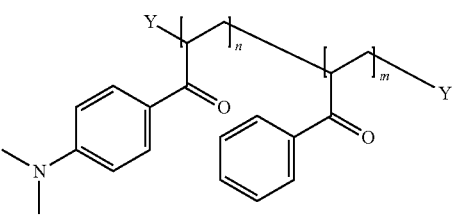 Example 5 | — | 46.0 | — |
| Total: | 100.0 | 100.0 | 100.0 |
| Viscosity (Pa.s.) @ 50 l/s | 21.08 | 25.14 | 105.2 |

TABLE 6

Composition and properties of inks

| Starting materials | Black ink 1 [%] | Black ink 2 [%] | Black ink 3 [%] |
|---|---|---|---|
| Varnish 1 (comparative) | 46.4 | — | 20.0 |
| Varnish 2 | — | 50.0 | — |
| Varnish 3 | — | — | 30.0 |
| Mixture of tetra- and hexafunctional acrylates (3:1) (Sun) | 13.3 | 20.9 | 20.9 |
| Stabilizer (Kromachem) | 1.0 | 1.0 | 1.0 |
| Leveling agent (Tego) | 0.5 | 0.5 | 0.5 |
| Blue Additive (Sun) | 0.7 | 0.7 | 0.7 |
| Inorganic Filler (Emerys) | 3.0 | 3.0 | 3.0 |
| Low migration photoinitiator blend based on oligomeric derivatives of aminobenzoates, benzophenones and thioxanthones | 9.1 | — | — |
| Irgacure 369 (BASF) | 2.1 | — | — |
| Oligomeric sensitizer (IGM) | 4.8 | 4.8 | 4.8 |
| Black pigment blend (Sun) | 19.1 | 19.1 | 19.1 |
| Total: | 100.0 | 100.0 | 100.0 |
| Viscosity @50 s$^{-1}$ (Pa · s.) | 28.94 | 42.29 | 23.63 |
| Tack 150 | 248 | 316 | 221 |

The present invention has now been described in detail, including the preferred embodiments thereof. However, it will be appreciated that those skilled in the art, upon consideration of the present disclosure, may make modifications and/or improvements on this invention that fall within the scope and spirit of the invention.

We claim:

1. An aminoketone of the general Formula I:

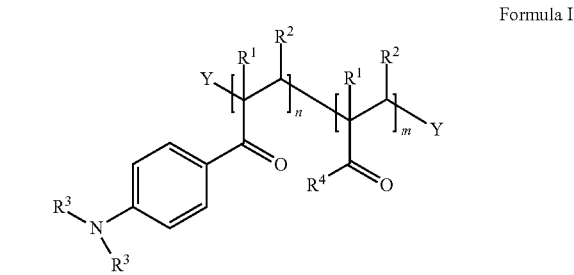

Formula I wherein

R$^1$ and R$^2$ are each independently selected from the group consisting of H, a branched or unbranched C$_{1-12}$ alkyl, and a C$_{3-12}$ aryl radical;

Each R$^3$ is independently selected from a branched or unbranched C$_{1-12}$ alkyl, or C$_{3-12}$ cycloalkyl radical; each of which is independently optionally substituted with R$^7$;

R$^4$ is selected from the group consisting of a branched or unbranched C$_{1-12}$ alkyl, C$_{3-12}$ aryl, and C$_{3-12}$ cycloalkyl radical; each of which is independently optionally substituted with R$^7$;

R$^7$ is selected from the group consisting of oxygen, nitrogen, and sulfur;

Each Y is a chain ending group, independently selected from H, or a methylol group;

n denotes an integer from 1-50; and m denotes an integer from 1-50.

2. A UV-curable composition comprising one or more aminoketones of claim 1, and one or more acrylates.

3. The composition of claim 2, which is a UV-curable coating or ink.

4. The UV-curable coating or ink of claim 3, that is curable with UV light having a wavelength of 310-400 nm.

5. The UV-curable coating or ink of claim 3, further comprising a colorant.

6. The UV-curable coating or ink according to claim 3, comprising no splitting type photoinitiators.

7. A low migration printed material comprising the coating or ink of claim 3.

8. A cured material, obtained by curing the UV-curable coating or ink of claim 3 with UV radiation.

* * * * *